United States Patent
Worley et al.

(10) Patent No.: US 10,487,038 B2
(45) Date of Patent: Nov. 26, 2019

(54) PROCESS FOR PURIFICATION OF METHYL METHACRYLATE

(71) Applicants: Rohm and Haas Company, Collegeville, PA (US); Dow Global Technologies LLC, Midland, MI (US)

(72) Inventors: William G. Worley, Missouri City, TX (US); Stacy W. Hoy, IV, Houston, TX (US)

(73) Assignees: Dow Global Technologies LLC, Midland, MI (US); Rohm and Haas, Philadelphia, PA (US)

( * ) Notice: Subject to any disclaimer, the term of this patent is extended or adjusted under 35 U.S.C. 154(b) by 0 days.

(21) Appl. No.: 15/776,850

(22) PCT Filed: Dec. 8, 2016

(86) PCT No.: PCT/US2016/065490
§ 371 (c)(1),
(2) Date: May 17, 2018

(87) PCT Pub. No.: WO2017/105977
PCT Pub. Date: Jun. 22, 2017

(65) Prior Publication Data
US 2018/0346403 A1 Dec. 6, 2018

Related U.S. Application Data

(60) Provisional application No. 62/269,461, filed on Dec. 18, 2015.

(51) Int. Cl.
*C07C 67/54* (2006.01)
*C07C 69/54* (2006.01)
*C07C 29/80* (2006.01)
*C07C 31/04* (2006.01)
*B01D 3/14* (2006.01)

(52) U.S. Cl.
CPC ............ *C07C 67/54* (2013.01); *B01D 3/143* (2013.01); *C07C 29/80* (2013.01); *B01D 2257/702* (2013.01); *C07C 31/04* (2013.01); *C07C 69/54* (2013.01)

(58) Field of Classification Search
CPC .......... C07C 67/54; C07C 29/80; B01D 3/143
See application file for complete search history.

(56) References Cited

U.S. PATENT DOCUMENTS

| | | | | |
|---|---|---|---|---|
| 3,431,181 A | * | 3/1969 | Bouniot | C07C 67/54 203/18 |
| 4,518,462 A | | 5/1985 | Aoshima et al. | |
| 5,028,735 A | * | 7/1991 | Segawa | C07C 29/88 203/37 |
| 5,435,892 A | | 7/1995 | Miyazaki et al. | |

FOREIGN PATENT DOCUMENTS

| | | |
|---|---|---|
| CN | 103833551 A | 6/2014 |
| JP | 2582127 B2 | 2/1997 |
| JP | 3819419 B2 | 9/2006 |

OTHER PUBLICATIONS

Wahnschafft et al (Industrial & Chemical Industry Research, A Problem Decomposition Approach for the Synthesis of Complex Separation Processes with Recycles, 1993, 32, pp. 1121-1141. (Year: 1993).*
Wu, et al., "Design and Control of a Methyl Methacrylate Separation Process with a Middle Decanter", Ind. Eng. Chem. Res, vol. 50, pp. 4595-4607 (2011).

* cited by examiner

Primary Examiner — Paul A Zucker
(74) Attorney, Agent, or Firm — Brian L. Mutschler

(57) ABSTRACT

A process for purifying methyl methacrylate by (a) feeding a mixture comprising methyl methacrylate and its alkali salt into a distillation column above the middle along with a hydrocarbon; (b) removing a first overhead stream; (c) removing a first bottoms stream; (d) feeding the first overhead stream to a first water separator to produce (i) a first organic phase and (ii) a first aqueous phase which enters a methanol drying column which produces a second overhead stream and a second bottoms stream; (e) feeding the first bottoms stream to a second water separator to produce (i) a second aqueous phase which is fed to an MMA stripper column which produces a third overhead stream and a third bottoms stream, and (ii) a second organic phase; (f) combining the second organic phase and the second bottoms stream into a third water separator which produces a third organic phase which enters an MMA drying column which produces a fourth bottoms stream, and (g) feeding the fourth bottoms stream to an MMA product column.

9 Claims, 1 Drawing Sheet

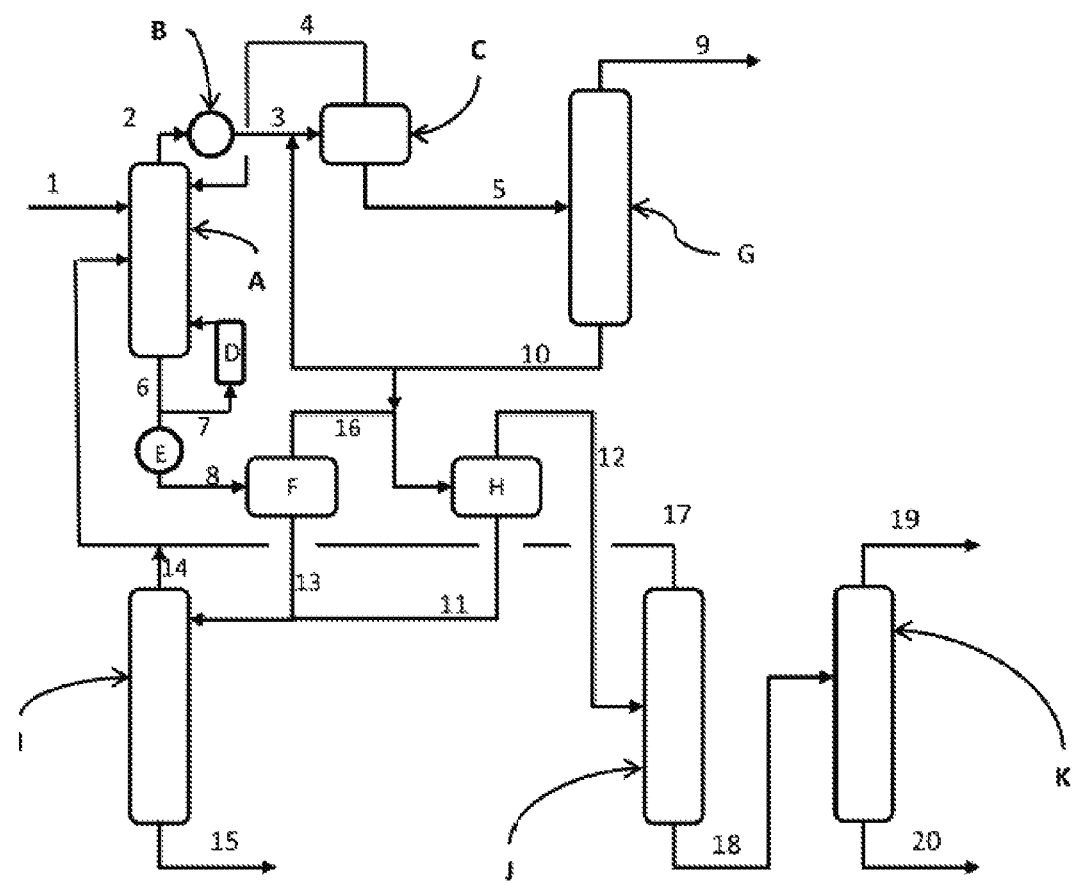

PROCESS FOR PURIFICATION OF METHYL METHACRYLATE

BACKGROUND OF THE INVENTION

The invention relates to an integrated process for purification of a methyl methacrylate (MMA) reaction product from the effluent of an oxidative esterification reactor (OER).

The use of oxidative esterification to prepare MMA from methacrolein and methanol is well known. For example, U.S. Pat. No. 4,518,462 discloses a process having a methanol recovery column using hexane as an entrainer. However, this process is not suitable for reaction products which contain MMA salts. There is a need for a more efficient process for separating the components of reaction products resulting from preparation of methyl methacrylate.

SUMMARY OF THE INVENTION

The present invention is directed to a process for purifying methyl methacrylate; said method comprising: (a) feeding a reaction product mixture comprising methanol, methyl methacrylate and alkali metal salts thereof, methacrolein, water and heavy byproducts to a first distillation column having at least 15 trays; wherein said reaction product mixture and a $C_6$-$C_7$ hydrocarbon enter the first distillation column above the middle of the distillation column; (b) removing a first overhead stream comprising $C_6$-$C_7$ hydrocarbon, methacrolein, methanol, water and methyl methacrylate; (c) removing a first bottoms stream comprising water, methyl methacrylate and alkali metal salts thereof and heavy byproducts; (d) feeding the first overhead stream to a first water separator to produce (i) a first organic phase which is returned to the first distillation column and (ii) a first aqueous phase which enters a methanol drying distillation column which produces a second overhead stream rich in methanol and a second bottoms stream which is rich in water, and at least a portion of said second bottoms stream is fed to the first water separator; (e) feeding the first bottoms stream to a second water separator to produce (i) a second aqueous phase which is fed to an MMA stripper distillation column which produces a third overhead stream rich in water and a third bottoms stream comprising water and methyl methacrylate alkali metal salt, and (ii) a second organic phase; (f) combining the second organic phase and the second bottoms stream into a third water separator which produces (i) a third organic phase which enters an MMA drying distillation column which produces a fourth overhead stream and a fourth bottoms stream, and (ii) a third aqueous phase; and (g) feeding the fourth bottoms stream to an MMA product distillation column which produces an MMA product stream and a bottoms stream.

BRIEF DESCRIPTION OF THE DRAWING

The FIGURE is a schematic of a process of the invention.

DETAILED DESCRIPTION OF THE INVENTION

All percentage compositions are weight percentages (wt %), and all temperatures are in ° C., unless otherwise indicated. Heavy byproducts are byproducts of the OER which have higher boiling points than methyl methacrylate, and which comprise oligomers of methyl methacrylate in addition to unknown products. Oligomers of methyl methacrylate comprise the dimer of methyl methacrylate and smaller amounts of higher oligomers, including, e.g., the trimer. Preferably, alkali metal salts are sodium or potassium salts, preferably sodium.

The $C_6$-$C_7$ hydrocarbon functions as an entrainer. It is believed that it breaks the methanol/MMA azeotrope, allowing removal and recovery of methanol in the first distillation column. Preferably, the $C_6$-$C_7$ hydrocarbon is aliphatic. Preferably, the $C_6$-$C_7$ hydrocarbon is a saturated hydrocarbon, preferably an acyclic alkane. In one preferred embodiment, a mixture of $C_6$-$C_7$ hydrocarbons is used. Preferably, the $C_6$-$C_7$ hydrocarbon or mixture thereof has an atmospheric pressure (101 kPa) boiling point from 65 to 100° C., preferably at least 67° C.; preferably no greater than 90° C., preferably no greater than 80° C., preferably no greater than 75° C. Preferably, the $C_6$-$C_7$ hydrocarbon is n-hexane.

Preferably, the first distillation column (methanol recovery column) has at least 20 trays, preferably at least 25; preferably no more than 40 trays, preferably no more than 35 trays. Preferably, the point at which the reaction product mixture enters the first distillation column is in the highest 40% of the trays, preferably the highest 30%, preferably the highest 20%, preferably the highest 10%, preferably the highest 7%. Preferably, the point at which the reaction product mixture enters the first distillation column is in the highest ten trays, preferably in the highest eight trays, preferably in the highest six trays, preferably in the highest four trays, preferably in the highest three trays, preferably in the highest two trays, preferably in the top stage.

Preferably, the methanol drying distillation column has from 20 to 40 trays; preferably at least 25, preferably at least 27; preferably no more than 35, preferably no more than 33. Preferably, the MMA stripper distillation column has from 5 to 30 trays; preferably at least 10, preferably at least 12; preferably no more than 25, preferably no more than 20. Preferably, the MMA drying distillation column has from 20 to 40 trays; preferably at least 25, preferably at least 27; preferably no more than 35, preferably no more than 33. Preferably, the MMA product distillation column has from 10 to 30 trays; preferably at least 15, preferably at least 17; preferably no more than 25, preferably no more than 23.

Preferably, the reaction product mixture comprises at least 0.8 wt % methyl methacrylate alkali metal salts, preferably at least 1 wt %, preferably at least 1.5 wt %, preferably at least 1.8 wt %; preferably no more than 3 wt %, preferably no more than 2.5 wt %, preferably no more than 2 wt %. Preferably, the reaction product mixture comprises from 40 to 80 wt % methanol, preferably from 45 to 70 wt %, preferably from 50 to 68 wt %. Preferably, the reaction product mixture comprises from 5 to 40 wt % methyl methacrylate, preferably from 10 to 35 wt %, preferably from 15 to 32 wt %. Preferably, the reaction product mixture comprises from 1 to 10 wt % water, preferably from 3 to 9 wt %, preferably from 4 to 8 wt %. Preferably, the amount of the $C_6$-$C_7$ hydrocarbon(s) which enters the first distillation column as reflux is from 2 to 10 times the amount of methanol in the product mixture, preferably 3 to 5 times. Preferably, when additional $C_6$-$C_7$ hydrocarbon needs to be added, it enters the first distillation column in the highest ten trays, preferably in the highest eight trays, preferably in the highest six trays, preferably in the highest four trays, preferably in the highest three trays, preferably in the highest two trays, preferably in the top tray.

In a preferred embodiment, prior to the process described herein, the direct product from the OER passes through an initial distillation column to remove an initial overhead stream comprising light components, i.e., those having higher vapor pressure than methanol. The light components principally comprise methyl formate. Typical levels of methyl formate in the direct product are from 1 to 6 wt % and the initial bottoms stream from the initial distillation column is fed to the first distillation column as the reaction product mixture, which typically contains no more than 1 wt % methyl formate.

The first overhead stream passes through a condenser and then enters a first water separator, from which the first organic phase is returned to the same section of the first distillation column where the product mixture enters, and the first aqueous phase is sent to a methanol drying column. Preferably, the first aqueous phase comprises 50-68% water, 30-44% methanol and 2-6% methacrolein. Preferably, the first organic phase comprises 82-92% $C_6$-$C_7$ hydrocarbon, 4-10% methacrolein and 2-10% MMA. At least a portion of the second bottoms stream, which is rich in water, is added to the first overhead stream before it enters the first water separator. Preferably, the amount of water added to the first overhead stream is 0.2 to 1 times the amount of the overhead stream, preferably 0.25 to 0.6 times. Preferably, the first bottoms stream enters a second water separator after passing through a heat exchanger to cool it, preferably to a temperature no greater than 50° C., preferably from 20 to 50° C. The second organic phase is predominantly MMA (preferably 86-96%), with the remainder comprising mostly water (1-4%) and heavy byproducts (3-10%), and is processed further to obtain high-purity MMA. The second organic phase is combined with at least a portion of the second bottoms stream and sent to the third water separator, from which a third organic phase is sent to an MMA drying distillation column and a third aqueous phase is produced. Preferably, the third aqueous phase is combined with the second aqueous phase being sent to the MMA stripper column.

The first aqueous phase is fed to a methanol drying column to remove water. Preferably, the second overhead stream from this column comprises 82-92% methanol, 7-14% methacrolein and 0-4% MMA. Preferably, the second overhead stream is recycled to the OER.

The second aqueous phase contains methyl methacrylate alkali metal salt and water, preferably 70-90% water and 10-30% sodium MMA, as well as small amounts (0-2%) of MMA and methanol. The second aqueous phase enters an MMA stripper column which produces a third overhead stream rich in water and preferably comprising MMA (5-15%) and a small amount of methanol (2-6%). Preferably, the third overhead stream is sent to the first distillation column along with the product mixture.

The MMA drying column removes water from the crude MMA. Preferably, the fourth overhead stream from this column comprises 75-85% MMA, 15-22% water and 0-3% methanol. Preferably, the fourth overhead stream is sent to the first distillation column, preferably to the middle third of the column, preferably below the point at which the reaction product mixture enters the column. Preferably, the fourth bottoms stream from this column comprises 90-96% MMA and 4-10% heavy byproducts. The fourth bottoms stream is fed to an MMA product distillation column which removes the heavy byproducts to produce an MMA overhead stream which preferably is 99-100% purity and a fifth bottoms stream which comprises MMA and heavy byproducts.

Water may be decanted from a stream by the means of standard methods. In one preferred embodiment, by means of a vessel that contains a vertical baffle or a series of baffles and is sized sufficiently that the organic and aqueous phase separate into individual phases. The lighter phase organic proceeds over the vertical baffle and the heavier water phase flows underneath the baffle. The separated liquids are withdrawn from the sections of the vessel that have accumulated the overflow and underflow of each phase.

Preferably, polymerization inhibitor is added to one or more of the columns to minimize polymerization of MMA. Amounts of inhibitor typically are small and types and typical use amounts are well known in the field.

The temperature and pressure in a distillation column is dependent on the composition of the material being distilled. In a preferred embodiment of the invention, the columns are operated at reduced pressure, such as from about 100 to about 760 mmHg (13 to 101 kPa), or from 200 to 400 mmHg (26 to 53 kPa). Preferably, the column pressure is adjusted to keep the bottoms temperature below 120° C., preferably below 100° C.

The FIGURE depicts a process flow diagram for the claimed process. reaction product mixture 1 is introduced into first distillation column A. A first bottom stream 6 from the column is split, with stream 8 passing through a heat exchanger E, and recycle 7 returned to the column through reboiler D. Overhead stream 2 leaves the column at the top and passes through condenser B and the resulting stream 3 enters water separator C, to produce (i) a first organic phase 4 which is returned to the first distillation column and (ii) a first aqueous phase 5 which enters methanol drying distillation column G which produces a second overhead stream 9 rich in methanol and a second bottoms stream 10 which is rich in water, and at least a portion of the second bottoms stream is fed to the first water separator. Stream 8 is fed to a second water separator F to produce (i) a second aqueous phase 13 which is fed to an MMA stripper distillation column I which produces a third overhead stream 14 rich in water and a third bottoms stream 15 comprising water and methyl methacrylate sodium salt, and (ii) a second organic phase 16. Second organic phase 16 and a portion of second bottoms stream 10 are fed into a third water separator H which produces (i) a third organic phase 12 which enters an MMA drying distillation column J which produces a fourth overhead stream 17 and a fourth bottoms stream 18, and (ii) a third aqueous phase 11. Fourth bottoms stream 18 is fed to an MMA product distillation column K which produces an MMA product stream 19 and a bottoms stream 20.

EXAMPLES

Example 1

This experiment is carried out using the process configuration shown in the FIGURE. The distillation column is a 28 mm i.d. 30-tray Oldershaw column, and n-hexane is employed as the entrainer solvent. A steam-heated thermosiphon reboiler is used to provide the boil-up in the column. The pressure at the top of the column is 700 mmHg absolute. The overhead temperature is 48° C., and the bottoms temperature is 83° C.

A mixture containing 29.9% MMA, 58.1% methanol, 2.1% methacrolein, 7.1% water, and 1.2% sodium methacrylate, with the balance being lights (higher vapor pressure than methanol) and organic heavies (lower vapor pressure than MMA) is fed through line 1 at a rate of 197 g/hr to the top tray of the distillation column.

Surprisingly, no salt precipitation is observed on the trays or in the reboiler after 8 hours of run time. No sodium methacrylate is detected in the bottoms organic crude MMA stream so, further downstream processes will have no difficulty with salt precipitation.

TABLE 1

Stream Compositions and Process Conditions for Ex. 1

| Component | 1 | 3 | 6 | 7 | 8 | 11 | 12 |
|---|---|---|---|---|---|---|---|
| Water | 7.10% | | 99.96% | 0.0% | 61.1% | 1.2% | 84.40% |
| Methanol | 58.10% | 99% | | 0.2% | 36.7% | | |
| Methacrolein | 2.10% | | | 1.6% | 0.7% | | |
| Methyl Methacrylate | 29.90% | | | 8.4% | 1.1% | 97.0% | 1.40% |
| Sodium Methacrylate | 1.20% | | | | | trace | 14.10% |
| Hexane | | | | 89.50% | | | |
| Phenothiazine | | 1% | | NA | NA | NA | NA |
| 4-Hydroxy Tempo | 0.04% | | 0.04% | NA | NA | NA | NA |
| Flow (g/hr) | 197.0 | 5.0 | 187.8 | 371.5 | 315.0 | 58.1 | 16.8 |

NA—not applicable

Example 2

An ASPEN simulation of feed location in a 30-tray first distillation column (tray 1 is the top tray), assuming 60% tray efficiency produced the following results for the % MMA recycled to that column.

| Feed Tray | % MMA Recycled |
|---|---|
| 1 | 5.6% |
| 6 | 7.3% |
| 11 | 7.4% |
| 16 | 8.0% |
| 21 | 9.8% |

The efficiency of the first column increases as the location of the reaction product mixture feed rises in the column.

The invention claimed is:

1. A process for purifying methyl methacrylate from effluent of an oxidative esterification reactor; said method comprising: (a) feeding a reaction product mixture comprising methanol, methyl methacrylate and alkali metal salts thereof, methacrolein, water and heavy byproducts to a first distillation column having at least 15 trays; wherein said reaction product mixture and a $C_6$-$C_7$ hydrocarbon enter the first distillation column above the middle of the distillation column; (b) removing a first overhead stream comprising $C_6$-$C_7$ hydrocarbon, methacrolein, methanol, water and methyl methacrylate; (c) removing a first bottoms stream comprising water, methyl methacrylate and alkali metal salts thereof and heavy byproducts; (d) feeding the first overhead stream to a first water separator to produce (i) a first organic phase which is returned to the first distillation column and (ii) a first aqueous phase which enters a methanol drying distillation column which produces a second overhead stream rich in methanol and a second bottoms stream which is rich in water, and at least a portion of said second bottoms stream is fed to the first water separator; (e) feeding the first bottoms stream to a second water separator to produce (i) a second aqueous phase which is fed to an MMA stripper distillation column which produces a third overhead stream rich in water and a third bottoms stream comprising water and methyl methacrylate alkali metal salt, and (ii) a second organic phase; (f) combining the second organic phase and the second bottoms stream into a third water separator which produces (i) a third organic phase which enters an MMA drying distillation column which produces a fourth overhead stream and a fourth bottoms stream, and (ii) a third aqueous phase; and (g) feeding the fourth bottoms stream to an MMA product distillation column which produces an MMA product stream and a bottoms stream.

2. The process of claim 1 wherein the reaction product mixture comprises at least 0.8 wt % of alkali metal salts of methyl methacrylate.

3. The process of claim 2 wherein the reaction product mixture comprises from 1 to 10 wt % water.

4. The process of claim 3 wherein the reaction product mixture enters the first distillation column in the highest 30% of the trays.

5. The process of claim 4 wherein $C_6$-$C_7$ hydrocarbon is a saturated hydrocarbon having an atmospheric pressure boiling point from 65 to 100° C.

6. The process of claim 5 wherein the fourth overhead stream is sent to the first distillation column in the middle third of the column.

7. The process of claim 6 wherein the reaction product mixture is an initial bottoms stream produced by sending a product from an oxidative esterification reactor to an initial distillation column which also produces an initial overhead stream comprising light components.

8. The process of claim 7 wherein the second overhead stream is recycled to the oxidative esterification reactor.

9. The process of claim 8 wherein the reaction product mixture enters the first distillation column within the highest six trays.

* * * * *